United States Patent [19]
Coufal et al.

[11] Patent Number: 5,883,875
[45] Date of Patent: Mar. 16, 1999

[54] SHORT COHERENT-LENGTH OPTICAL TOMOGRAPH FOR HIGH DENSITY VOLUME OPTICAL DATA STORAGE DEVICES

[75] Inventors: Hans Juergen Coufal, San Jose; Robert K. Grygier, San Diego, both of Calif.

[73] Assignee: International Business Machines Corporation, Armonk, N.Y.

[21] Appl. No.: 921,710

[22] Filed: Sep. 2, 1997

[51] Int. Cl.$^6$ .................................................. G11B 7/00
[52] U.S. Cl. ........................... 369/116; 369/54; 369/94; 369/112; 369/275.2
[58] Field of Search ............................ 369/116, 94, 54, 369/112, 275.2

[56] References Cited

U.S. PATENT DOCUMENTS

| | | | |
|---|---|---|---|
| 5,103,572 | 4/1992 | Ricklefs | 33/558 |
| 5,784,352 | 7/1998 | Swanson et al. | 369/94 |

OTHER PUBLICATIONS

S.R. Chinn et al., Multilayer optical storage using low-coherence reflectometry, CLEO '96, pp. 101–102, 1996.
R. Cassidy, Laser Feedback Microscope Offers Resolution Rivaling SEM, R&D Magazine, pp. 83–84, May 1995.
T.L. Wong et al., PHOEbE, a prototype scanning laser-feedback microscope for imaging biological cells in aqueous media, Journal of Microscopy, vol. 177, Pt 2, pp. 162–170, Feb. 1995.
A. Bearden et al., Imaging and vibrational analysis with laser-feedback interferometry, Optics Letters, vol. 18 No. 3, pp. 238–240, Feb. 1, 1993.
L. Wang et al., Kerr–Fourier imaging of hidden objects in thick turbid media, Optics Letters, vol. 18, No. 3, pp. 241–243, Feb. 1, 1993.

*Primary Examiner*—Tod R. Swann
*Assistant Examiner*—Kim-Kwok Chu
*Attorney, Agent, or Firm*—Morgan & Finnegan, L.L.P.

[57] ABSTRACT

A device for reading data from a multi-layered optical disk includes a short coherence-length light source, a beam splitter, an adjustable mirror and an optical detector. The beam splitter is used to form first and second light beams from the short coherence-length light beam. The first light beam is then directed to the optical disk and is reflected by a data mark stored on the optical disk. The second light beam is directed along a reference beam path. The mirror is disposed along the reference beam path and reflects the second light beam back to the beam splitter. The beam splitter recombines the reflected first light beam and the second light beam after the second light beam traverses the reference beam path. The optical detector detects the data mark by constructive interference of the combined reflected first light beam and the second light beam. The position of the mirror is adjustable so that the optical path length of the reference beam path is made equal to the optical path length of the first light beam to each layer of the multi-layered optical disk. A device for recording data onto a multi-layered optical disk uses similar components and techniques for recording data.

32 Claims, 6 Drawing Sheets

SHORT COHERENT-LENGTH OPTICAL TOMOGRAPH FOR HIGH DENSITY VOLUME OPTICAL DATA STORAGE DEVICES

BACKGROUND OF THE INVENTION

1. Field of the Invention

The present invention relates to the field of data storage. More particularly, the present invention relates to a device for recording and detecting data marks within a multi-layered storage media.

2. Description of the Related Art

Digital optical data storage devices, such as multi-layered optical disks, store information in the volume of a recording media, as well as at the surface of the media. Volume optical storage techniques have been demonstrated using multi-layered media by focusing a laser beam on individual layers within the media. Further, the ability to image objects buried within semi-transparent, turbid, or highly scattering material with a high-depth resolution is important for many optical tomography applications. For example, see H. Coufal, "Optical Tomography?," J. Mol. Structure, Vol. 347, 285 (1995). Previously, the ability to image buried objects could only be accomplished using a variety of time-gated optical imaging techniques requiring expensive picosecond or femtosecond lasers and fast optical detection techniques. For example, see L. Wang, P. O. Ho, X. Liang, H. Dai, and R. R. Alfano, "Kerr-Fourier Imaging of Hidden Objects in Thick Turbid Media," Optics Letters, Vol. 18, No. 3, Feb. 1, 1993, pp. 241–243. Interferometric methods have also been developed, such as laser-feedback interferometry, which detect perturbations caused by light scattered from a buried object reentering the laser cavity. For example, see Robert Cassidy, "Laser Feedback Microscope Offers Resolution Rivaling SEM," Research and Development, Vol. 37, No. 6, May 1995, pp. 83–84; T. L. Wong, S. L. Sabato, and A. Bearden, "PHOEBE a Prototype Scanning Laser-Feedback Microscope for Imaging Biological Cells in Aqueous Media," J. of Microscopy, Vol. 177, Pt. 2, February 1995, pp. 162–170; and A. Bearden, M. P. O'Neill, L. C. Osborne, and T. L. Wong, "Imaging and Vibrational Analysis with Laser-Feedback Interferometry," Optics Letters, Vol. 18, No. 3, Feb. 1, 1993, pp. 238–240. These conventional interferometric approaches, however, require a controlled feedback positioning system for mapping the buried interface and are similar to other scanning confocal microscopes.

What is needed is an inexpensive way for recording digital data onto a multi-layered optical disk and then for reading the recorded digital data.

SUMMARY OF THE INVENTION

The present invention provides an inexpensive way for recording digital data onto a multi-layered optical disk and for reading digital data that has been recorded onto a multi-layered optical disk. The present invention provides a high-depth resolution interferometer that directs light from a short coherence-length light source, such as an inexpensive light-emitting diode (LED) or diode laser, at an object buried within a multi-layer optical disk. The light reflected from the buried object is combined with a reference beam. According to the invention, the path length of the object beam and the path length of the reference beam are equal. Since the light has a short coherence-length, only the light reflected from a narrow depth at the buried object will interfere constructively with the light of the reference beam, allowing the object to be imaged. Light reflected from other depths will not interfere and, therefore, will have much lower contrast, as compared to the light reflected by the buried object. Additionally, marks can be written at various depths for optical recording by interfering two beams from different directions at the desired location, but with equal optical path lengths.

The advantages of the present invention are provided by a device for reading data from a multi-layered optical disk that includes a short coherence-length light source, a beam splitter, an adjustable mirror and an optical detector. The beam splitter is used to form first and second light beams from the short coherence-length light beam. The first light beam is then directed to the optical disk and is reflected by a data mark stored on the optical disk. The second light beam is directed along a reference beam path. The adjustable mirror is disposed along the reference beam path and reflects the second light beam back to the beam splitter. The beam splitter recombines the reflected first light beam and the second light beam after the second light beam traverses the reference beam path. The optical detector detects the data mark by constructive interference of the combined reflected first light beam and the second light beam. According to the invention, the position of the mirror is adjustable so that the optical path length of the reference beam path is made equal to the optical path length of the first light beam to each layer of the multi-layered optical disk. Preferably, an actuator, such as a voice coil or a piezo actuator, is used for adjusting the position of the mirror.

One embodiment of the invention provides an imaging lens disposed along an optical path of the combined reflected first light beam and the second light beam between the splitter and the optical detector so that an image of a plurality of data marks onto an optical detector array for simultaneously detecting a plurality of data marks from a predetermined layer of the optical disk. Another embodiment of the present invention provides a phase modulator, such as a liquid crystal device, disposed along an optical path of the reference beam between the splitter and the mirror. The phase modulator changes the optical path length of different parts of reference beam so that parallel data tracks in different predetermined layers are simultaneously detected by an optical detector array.

The present invention also provides a device for recording data on a multi-layered optical disk. The recording device includes a short coherence-length light beam, a beam splitter and an adjustable mirror. The beam splitter forms a reference light beam and an object light beam from the short coherence-length light beam. The reference light beam is directed along a reference beam path, while the object light beam is directed to a predetermined point of the optical disk. The mirror is disposed along the reference beam path and reflects the reference light beam back through the beam splitter. The reference light beam and object light beam constructively interfere at the predetermined point of the optical disk, thereby writing a data mark on the optical disk. According to the invention, the position of the mirror is adjustable by an actuator, such as a voice coil or a piezo actuator, so that the optical path length of the reference beam path is to equal the optical path length of the object light beam to each layer of the multi-layered optical disk.

A spatial light modulator, such as a liquid crystal device that encodes data into the object light beam, can be disposed along a beam path of the object light beam between the splitter and the optical disk. An imaging lens is then disposed along the beam path of the object light beam between the spatial light modulator and the optical disk so that an image of the object light beam is formed on a predetermined area of the optical disk. The reference light beam and object light beam constructively interfere at the predetermined area of the optical disk, thereby writing at least one data mark into at least one data track of a plurality of data tracks within the predetermined area. Additionally, a phase modulator, such as a liquid crystal device, can be disposed along the reference beam path between the splitter and the mirror. The phase modulator changes the optical path length of predetermined parts of the reference beam so that the reference light beam and object light beam constructively interfere at the predetermined area of the optical disk, thereby writing at least one data mark into at least one data track of at least one layer within the predetermined area.

While the present invention can be used for high-density optical data storage in multi-layer disks and volume optical data storage, the present invention can also be used for silicon wafer inspection, magnetic disk inspection, contamination control, surface roughness determination, process control, optical tomography, medical imaging, and military target recognition, for example.

BRIEF DESCRIPTION OF THE DRAWING

The present invention is illustrated by way of example and not limitation in the accompanying figures in which like reference numerals indicate similar elements and in which.

DETAILED DESCRIPTION

The present invention is an interferometer that uses a short coherence-length light source, such as a light-emitting diode (LED) or diode laser. For readout of the data bits, light from each data bit mark is interfered with a reference beam, with the path length of the data beam and the path length of the reference beam being equal. Since the light has a short coherence-length, only light reflected from a narrow depth at the buried data layer interferes constructively with the reference beam and allows the data to be detected and reconstructed. Light reflected from other depths does not interfere constructively and, therefore, has a much lower contrast as compared to the light reflected from the desired data layer. Data bits are written at various depths within a multi-layer optical disk by interfering two beams from different directions at the desired location, but with equal optical path lengths.

The present invention provides recording and readout of digital data within a thick optical storage media, such as high-density read only, WORM and rewritable optical storage devices. Additionally, the present invention has a variety of applications in optical tomography in which semi-transparent or scattering media are probed or imaged, for example, depth profiles of silicon wafers which are implanted, etched, or have buried defects can be fabricated using short coherence-length infrared light sources. Further, medical imaging can be performed using LEDs or laser diodes for generating an image of injured human limbs, providing an inexpensive and portable replacement for X-ray, MRI, and CAT-scan devices under certain circumstances. The present invention can also be used for creating a three-dimensional TV display device by interfering a beam containing a changing image with a reference beam within a solid matrix containing a fluorescing material.

Figure 1:
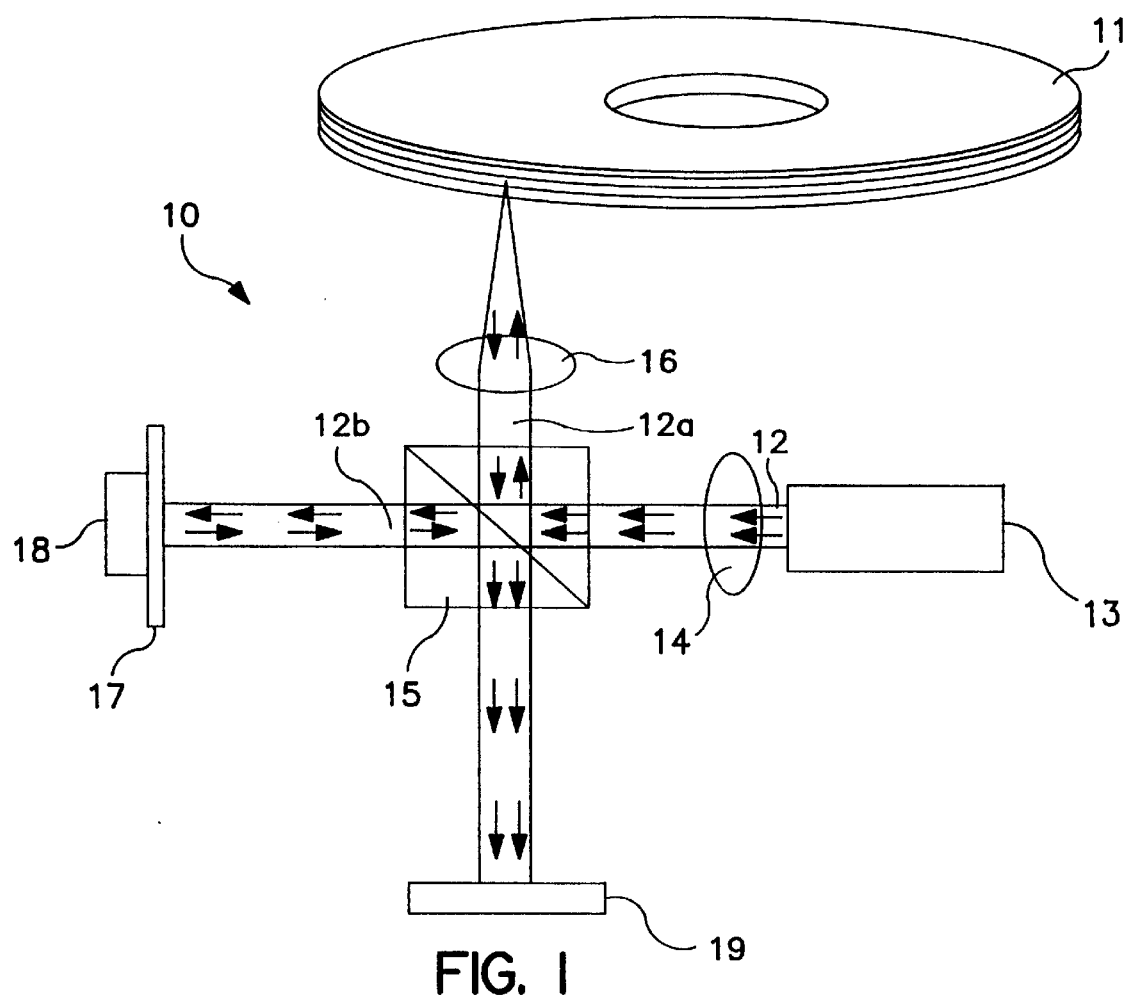
FIG. 1 shows an arrangement for readout of a single data track within a multi-layer optical disk according to the present invention.

FIG. 1 shows an arrangement 10 for readout of a single data track within a multi-layer optical disk 11. Light 12 from a short coherence-length light source 13 is collimated by collimating lens 14. The collimated light passes through a beam splitter 15 where an object beam portion 12a of the light is directed through a focusing and readout lens 16 to optical disk 11. A reference beam portion 12b of the light is directed to a movable mirror 17 which reflects the light back to beam splitter 15, which, in turn, directs the light to an optical detector 19. The readout of a data bit occurs when light reflected from the data bit mark stored on disk 11 is collected by focusing readout lens 16 and is directed to optical detector 19. Movable mirror 17 is positioned along the direction of reference beam 12b by an actuator 18, such as, a voice coil or a piezo actuator, until constructive interference is formed between the object beam and the reference beam, causing the data bit to have a high contrast. To read out a data bit that is located within another layer of disk 11, movable mirror 17 is adjusted until the light reflected from data bits located within the desired layer constructively interfere with the reference beam. Data located within adjacent layers are rejected because the marks forming the data are separated from the data marks within the desired layer by a distance which is greater than the coherence length of light source 13.

Figure 2:
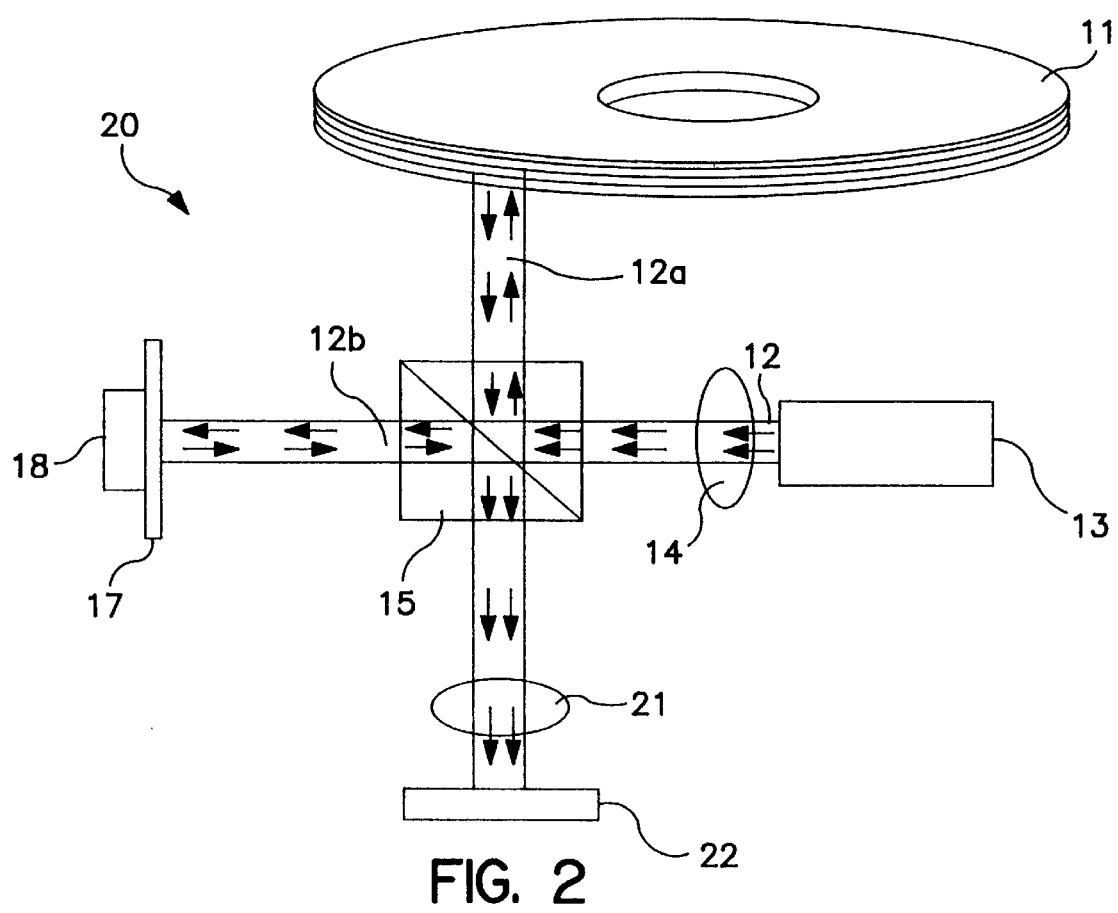
FIG. 2 shows an arrangement for readout of multiple data bits from a signal layer within a multi-layer optical disk according to the present invention.

FIG. 2 shows an arrangement 20 for readout of multiple data bits from a single layer within a multi-layer optical disk 11. Arrangement 20 is similar to arrangement 10 shown in FIG. 1, except that object beam 12a is directed to optical disk 11 without focusing. The reflected light is then imaged using an imaging lens 21 onto a CCD detector array 22, allowing multiple bits from a single layer to be simultaneously detected.

Figure 3:
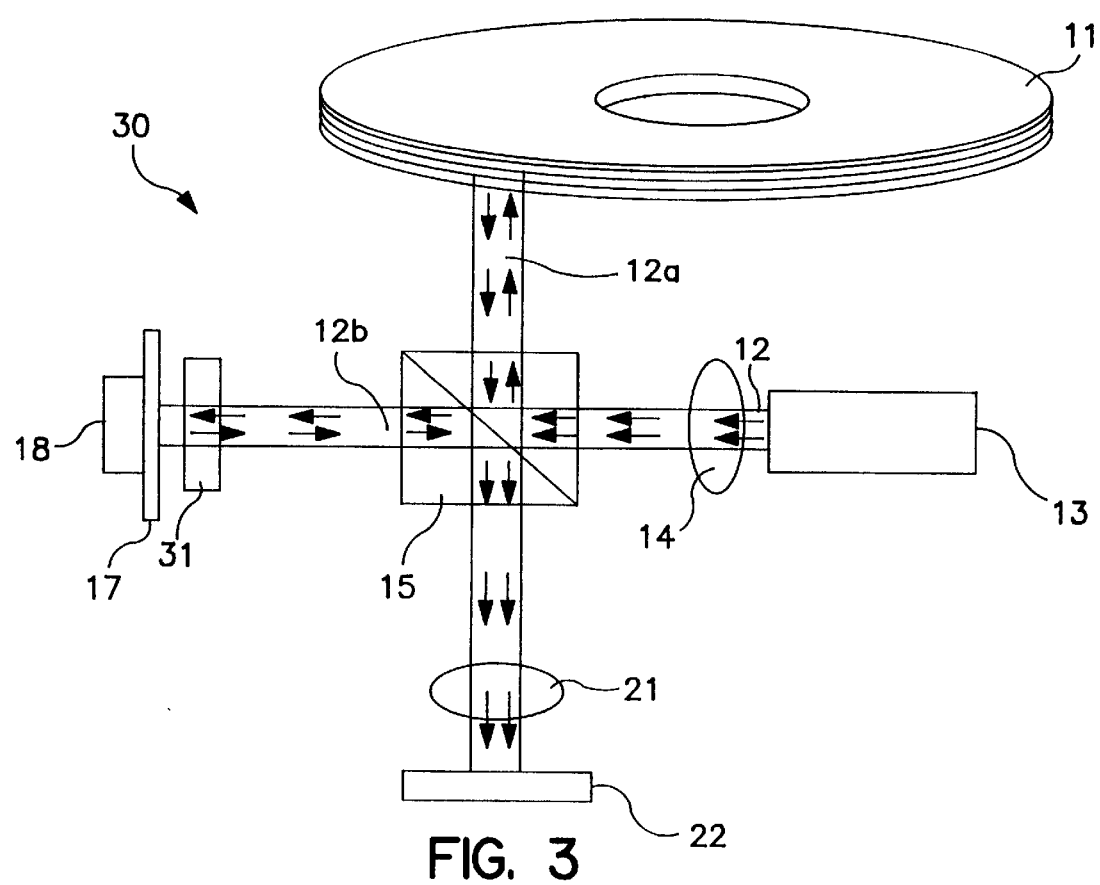
FIG. 3 shows an arrangement for simultaneous readout of multiple data layers from within a multi-layer optical disk according to the present invention.

FIG. 3 shows an arrangement 30 for simultaneous readout of multiple data layers from within a multi-layer optical disk 11. Arrangement 30 is similar to arrangement 20 shown in FIG. 2, except that a phase modulator 31 is introduced into the path of reference beam 12b for allowing simultaneous readout of several buried data layers within disk 11. Phase modulator 31 is an active element, such as a liquid crystal device, which changes the optical path length of different parts of reference beam 12b in a well-known manner so that parallel data tracks in different layers are simultaneously read out.

Figure 4:
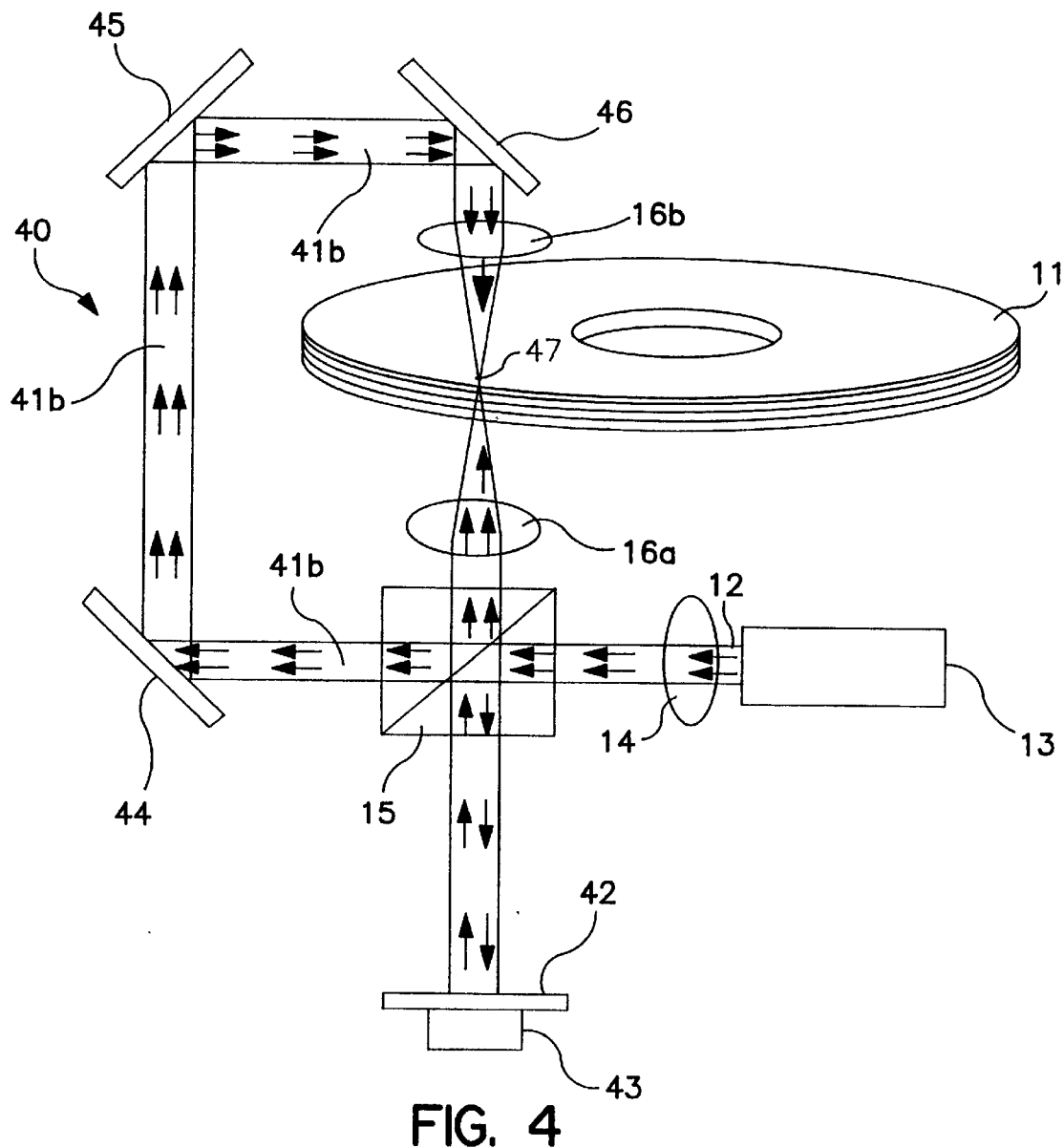
FIG. 4 shows an arrangement for writing a single data track within a multi-layer optical disk according to the present invention.

FIG. 4 shows an arrangement 40 for writing a single data track within a multi-layer optical disk 11. Arrangement 40 involves focusing two beams 41a and 41b from different directions onto a desired data layer within disk 11. Light 12 from a short coherence-length light source 13 is collimated by collimating lens 14. The collimated light passes through a beam splitter 15 where a first beam 41a is directed to a movable mirror 42. Beam 41a is reflected from mirror 42 and directed back through beam splitter 15 and a focusing lens 16a to a desired point 47 within optical disk 11 from one side of disk 11. Beam 41b passes through beam splitter 15 and is directed to the other side of disk 11 using mirrors 44, 45 and 46, and is focused at desired point 47 by focusing lens 16b. The optical path length for each beam 41a and 41b is made equal by using movable mirror 42. Movable mirror 42 is positioned along the direction of beam 41a by an actuator 43, such as, a voice coil or a piezo actuator. Beams 41a and 41b constructively interfere, creating a large light intensity and causing physical and/or chemical changes, depending upon the nature of the optical disk, at desired spot 47, thereby writing a data bit.

Figure 5:
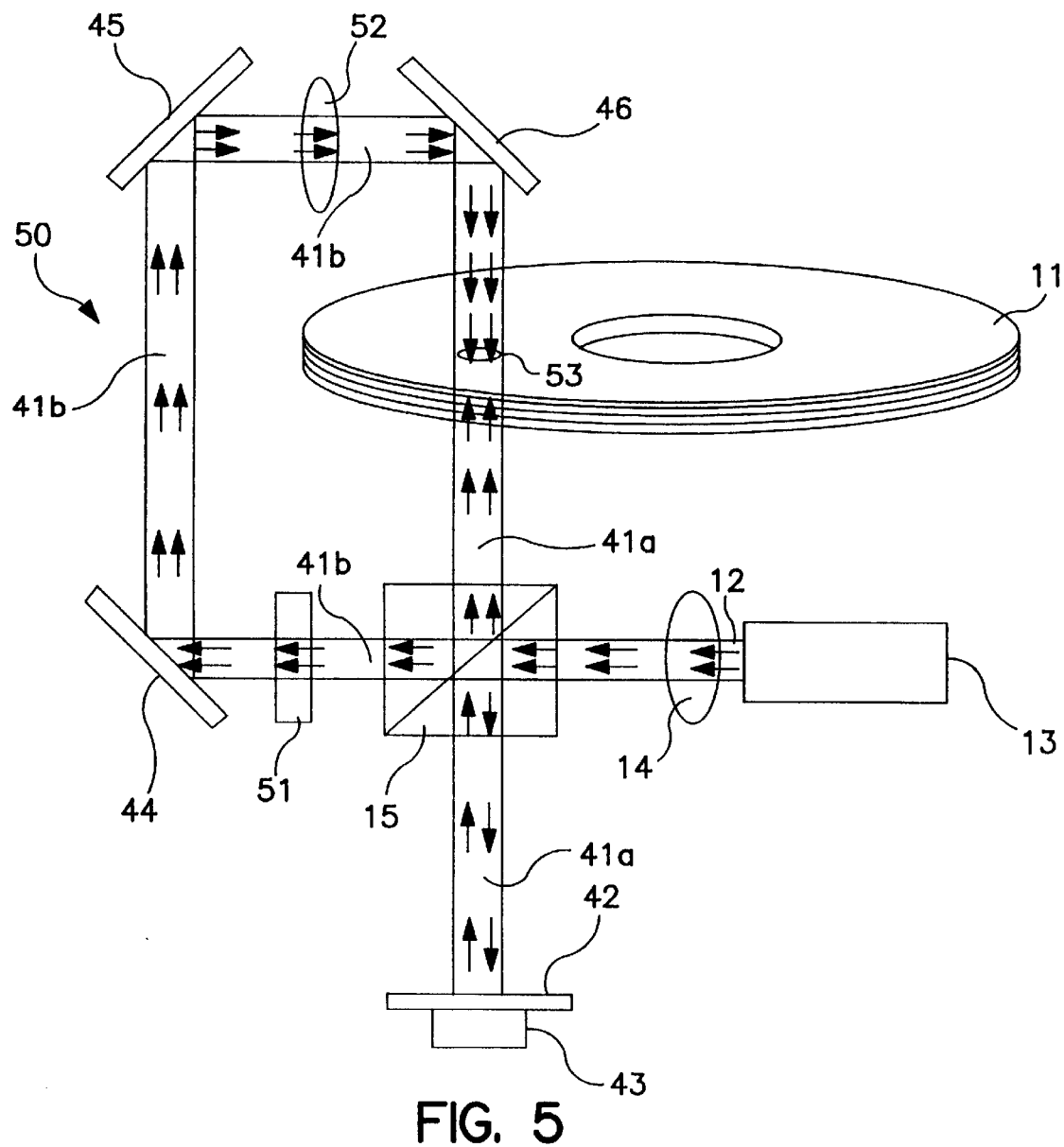
FIG. 5 shows an arrangement for simultaneously writing multiple-data tracks within a multi-layer optical disk according to the present invention.

FIG. 5 shows an arrangement 50 for simultaneously writing multipledata tracks within a multi-layer optical disk 11. Arrangement 50 utilizes two beams 41a and 41b, with beam 41a acting as a reference beam. Beam 41b has data encoded onto it in a well-known manner using a spatial light modulator 51, such as a liquid crystal device. Beam 41b is then imaged onto optical disk 11 using imaging lens 52. The optical path length for the both beams is made equal by using movable mirror 42 and actuator 43. Beams 41a and 41b constructively interfere, creating a large light intensity and causing physical and/or chemical changes, depending upon the nature of the optical disk, at spots within desired area 53, thereby writing data into multiple data tracks on the same layer.

Figure 6:
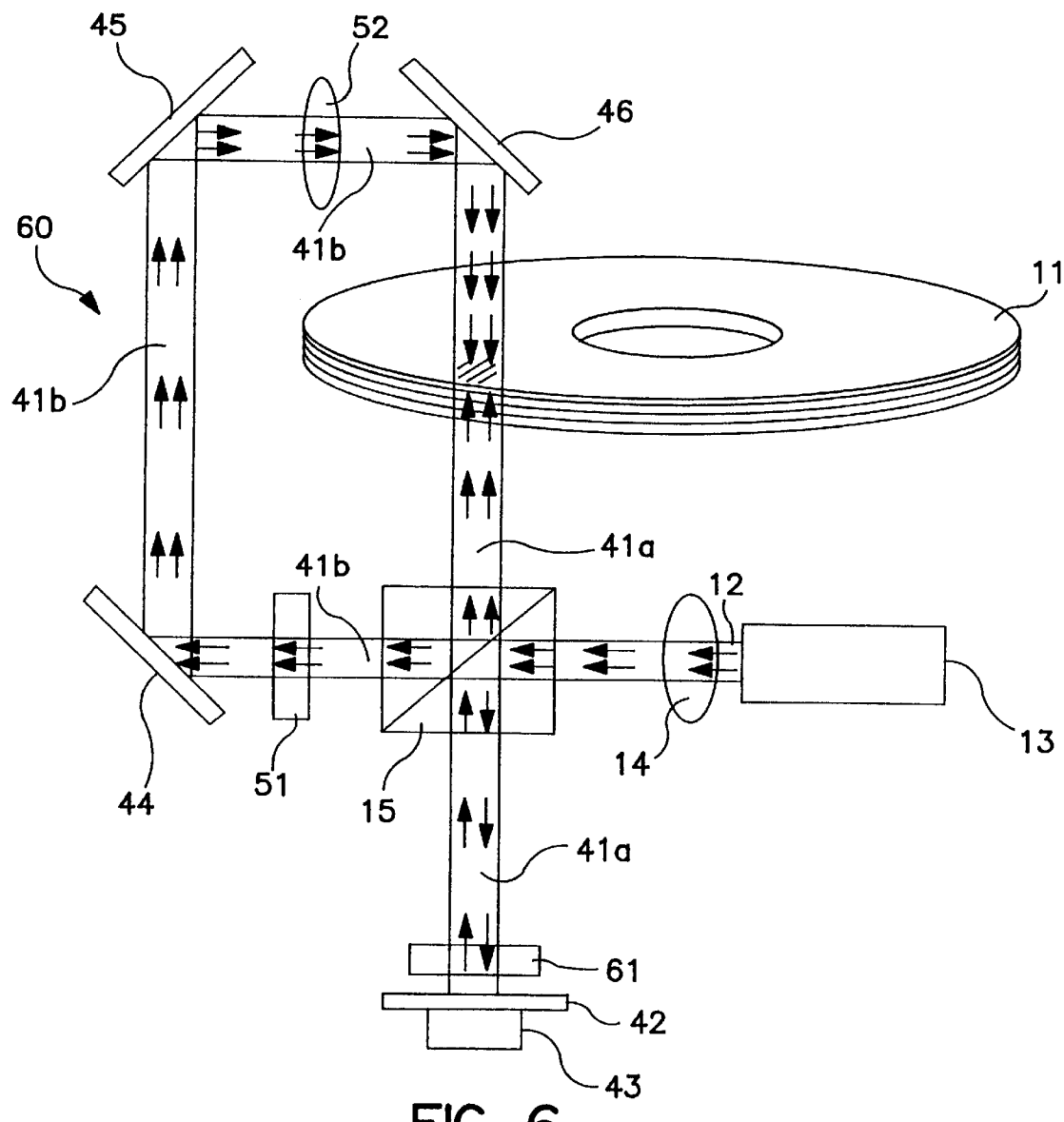
FIG. 6 shows an arrangement for writing multiple data layers within a multi-layer optical disk according to the present invention.

FIG. 6 shows an arrangement 60 for writing multiple data layers within a multi-layer optical disk 11. Arrangement 60 is similar to arrangement 50 shown in FIG. 5, except that a phase modulator 61 is inserted into the path of reference beam 41a. Phase modulator 61 is an active element, such as a liquid crystal device, that changes the optical path length of different parts of beam 41a in a well-known manner so that parallel data tracks in different layers can be simultaneously written.

Each of the data read out arrangements of FIGS. 1–3 can be combined with each of the data writing arrangments of FIGS. 4–6 for producing a device that both reads data from and writes data to a multi-layered optical disk.

While the present invention has been described in connection with the illustrated embodiments, it will be appreciated and understood that modifications may be made without departing from the true spirit and scope of the invention.

What is claimed is:

1. A device for reading data from an optical disk, the device comprising:
    a light source generating a short coherence-length light beam;
    a beam splitter forming first and second light beams from the short coherence-length light beam, the first light beam being directed to the optical disk and being reflected by a data mark stored on the optical disk, the second light beam being directed along a reference beam path, the beam splitter recombining the reflected first light beam and the second light beam after the second light beam traverses the reference beam path;
    an optical detector detecting the data mark by constructive interference of the combined reflected first light beam and the second light beam; and
    a mirror disposed along the reference beam path, the mirror reflecting the second light beam back to the beam splitter, a position of the mirror defining an optical path length of the reference beam path to be equal to an optical path length of the first light beam.

2. The device according to claim 1, wherein the optical disk is a multi-layered optical disk, each layer being capable of storing a data mark,
    wherein the position of the mirror is adjustable so that the optical path length of the reference beam path to equal the optical path length of the first light beam to each layer of the multi-layered optical disk.

3. The device according to claim 2, wherein the mirror includes an actuator for adjusting the position of the mirror.

4. The device according to claim 3, wherein the actuator includes a voice coil.

5. The device according to claim 3, wherein the actuator includes a piezo actuator.

6. The device according to claim 1, wherein the optical disk is a multi-layered optical disk, each layer being capable of storing a data mark, and
    wherein the optical detector is an optical detector array,
    the device further comprising an imaging lens disposed along an optical path of the combined reflected first light beam and the second light beam between the splitter and the optical detector, the imaging lens imaging a plurality of data marks onto the optical detector array for simultaneously detecting a plurality of data marks from a predetermined layer of the optical disk.

7. The device according to claim 6, wherein the position of the mirror is adjustable so that the optical path length of the reference beam path to equal the optical path length of the first light beam to each layer of the multi-layered optical disk.

8. The device according to claim 1, wherein the optical disk is a multi-layered optical disk, each layer being capable of storing a data mark, and
    wherein the optical detector is an optical detector array,
    the device further comprising a phase modulator disposed along an optical path of the reference beam between the splitter and the mirror, the phase modulator changing the optical path length of different parts of reference beam so that parallel data tracks in different predetermined layers are simultaneously detected by the optical detector.

9. The device according to claim 8, wherein the position of the mirror is adjustable so that the optical path length of the reference beam path to equal the optical path length of the first light beam to each layer of the multi-layered optical disk.

10. The device according to claim 9, wherein the phase modulator is a liquid crystal device.

11. The device according to claim 1, further comprising:
    a write beam splitter forming a write reference light beam and an object light beam from the short coherence-length light beam, the write reference light beam being directed along a reference beam path, the object light beam being directed to a predetermined point of the optical disk; and
    a write mirror disposed along the write reference beam path, the write mirror reflecting the write reference light beam back through the write beam splitter, a position of the write mirror defining an optical path length of the write reference beam path to be equal to an optical path length of the object light beam, the write reference light beam and object light beam constructively interfering at the predetermined point of the optical disk, thereby writing a data mark on the optical disk.

12. The device according to claim 11, wherein the optical disk is a multi-layered optical disk, each layer being capable of storing a data mark,
    wherein the position of the write mirror is adjustable so that the optical path length of the write reference beam path to equal the optical path length of the object light beam to each layer of the multi-layered optical disk.

13. The device according to claim 12, wherein the write mirror includes an actuator for adjusting the position of the write mirror.

14. The device according to claim 13, wherein the actuator includes a voice coil.

15. The device according to claim 13, wherein the actuator includes a piezo actuator.

16. The device according to claim 11, wherein the optical disk is a multi-layered optical disk, each layer having at least one data track, each track being capable of storing at least one data mark, the device further comprising:
a spatial light modulator disposed along a beam path of the object light beam between the write beam splitter and the optical disk, the spatial light modulator encoding data onto the object light beam; and
an imaging lens disposed along the beam path of the object light beam between the spatial light modulator and the optical disk, the imaging lens imaging the object light beam onto a predetermined area of the optical disk, the write reference light beam and object light beam constructively interfering at the predetermined area of the optical disk, thereby writing at least one data mark into at least one data track of a plurality of data tracks within the predetermined area, the at least one data mark corresponding to the data encoded onto the object light beam.

17. The device according to claim 16, wherein the light modulator is a liquid crystal device.

18. The device according to claim 17, wherein the position of the write mirror is adjustable so that the optical path length of the write reference beam path to equal the optical path length of the object light beam to each layer of the multi-layered optical disk.

19. The device according to claim 17, further comprising a phase modulator disposed along the write reference beam path between the write beam splitter and the mirror, the phase modulator changing the optical path length of predetermined parts of the write reference light beam so that the write reference light beam and object light beam constructively interfere at the predetermined area of the optical disk, thereby writing at least one data mark into at least one data track of at least one layer within the predetermined area, the at least one data mark corresponding to the data encoded onto the object light beam.

20. The device according to claim 19, wherein the phase modulator is a liquid crystal device.

21. The device according to claim 20, wherein the position of the write mirror is adjustable so that the optical path length of the write reference beam path to equal the optical path length of the object light beam to each layer of the multi-layered optical disk.

22. A device for recording data on an optical disk, the device comprising:
a light source generating a short coherence-length light beam;
a beam splitter forming a reference light beam and an object light beam from the short coherence-length light beam, the reference light beam being directed along a reference beam path, the object light beam being directed to a predetermined point of the optical disk; and
a mirror disposed along the reference beam path, the mirror reflecting the reference light beam back through the beam splitter, a position of the mirror defining an optical path length of the reference beam path to be equal to an optical path length of the object light beam, the reference light beam and object light beam constructively interfering at the predetermined point of the optical disk, thereby writing a data mark on the optical disk.

23. The device according to claim 22, wherein the optical disk is a multi-layered optical disk, each layer being capable of storing a data mark, wherein the position of the mirror is adjustable so that the optical path length of the reference beam path to equal the optical path length of the object light beam to each layer of the multi-layered optical disk.

24. The device according to claim 23, wherein the mirror includes an actuator for adjusting the position of the mirror.

25. The device according to claim 24, wherein the actuator includes a voice coil.

26. The device according to claim 25, wherein the actuator includes a piezo actuator.

27. The device according to claim 22, wherein the optical disk is a multi-layered optical disk, each layer having at least one data track, each track being capable of storing at least one data mark, the device further comprising:
a spatial light modulator disposed along a beam path of the object light beam between the splitter and the optical disk, the spatial light modulator encoding data onto the object light beam; and
an imaging lens disposed along the beam path of the object light beam between the spatial light modulator and the optical disk, the imaging lens imaging the object light beam onto a predetermined area of the optical disk, the reference light beam and object light beam constructively interfering at the predetermined area of the optical disk, thereby writing at least one data mark into at least one data track of a plurality of data tracks within the predetermined area, the at least one data mark corresponding to the data encoded onto the second light beam.

28. The device according to claim 27, wherein the light modulator is a liquid crystal device.

29. The device according to claim 28, wherein the position of the mirror is adjustable so that the optical path length of the reference beam path to equal the optical path length of the object light beam to each layer of the multi-layered optical disk.

30. The device according to claim 28, further comprising a phase modulator disposed along the reference beam path between the splitter and the mirror, the phase modulator changing the optical path length of predetermined parts of the reference beam so that the reference light beam and object light beam constructively interfere at the predetermined area of the optical disk, thereby writing at least one data mark into at least one data track of at least one layer within the predetermined area, the at least one data mark corresponding to the data encoded onto the second light beam.

31. The device according to claim 30, wherein the phase modulator is a liquid crystal device.

32. The device according to claim 31, wherein the position of the mirror is adjustable so that the optical path length of the reference beam path to equal the optical path length of the object light beam to each layer of the multi-layered optical disk.

* * * * *